United States Patent [19]

Roby et al.

[11] Patent Number: 5,919,893
[45] Date of Patent: Jul. 6, 1999

[54] POLYESTERAMIDE, ITS PREPARATION AND SURGICAL DEVICES FABRICATED THEREFROM

[75] Inventors: Mark S. Roby, Killingworth; Ying Jiang, North Haven, both of Conn.

[73] Assignee: United States Surgical Corporation, Norwalk, Conn.

[21] Appl. No.: 09/014,798

[22] Filed: Jan. 28, 1998

Related U.S. Application Data

[60] Provisional application No. 60/036,536, Jan. 28, 1997, abandoned.

[51] Int. Cl.⁶ .................................................. C08G 69/44
[52] U.S. Cl. .......................... 528/310; 528/170; 528/322; 528/323; 528/327; 528/354; 528/355; 528/361; 525/411; 525/415; 525/417; 606/139; 606/228; 606/230
[58] Field of Search ...................... 528/310, 170, 528/354, 355, 323, 327; 525/417, 415, 411; 606/228, 230, 139

[56] References Cited

U.S. PATENT DOCUMENTS

| | | | |
|---|---|---|---|
| Re. 30,170 | 12/1979 | Goodman et al. ...................... | 528/327 |
| 2,386,454 | 10/1945 | Frosch ........................................ | 260/78 |
| 4,226,243 | 10/1980 | Shalaby ................................ | 128/335.5 |
| 4,343,931 | 8/1982 | Barrows ................................... | 528/291 |
| 5,349,045 | 9/1994 | Jiang ....................................... | 528/323 |
| 5,446,108 | 8/1995 | Jiang ....................................... | 528/417 |
| 5,483,009 | 1/1996 | Jiang ....................................... | 525/417 |

*Primary Examiner*—P. Hampton-Hightower

[57] ABSTRACT

Degradable polyesteramide suitable for use in biomedical applications is obtained by reacting diamino alkyl ester with alpha hydroxy acid to form diamide-diol which is reacted with acyl halide or dicarboxylic acid to yield polyesteramide.

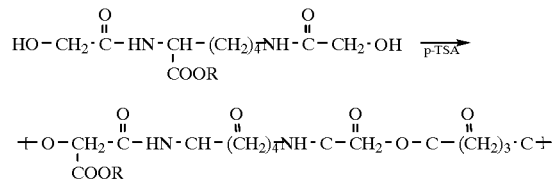

16 Claims, No Drawings

POLYESTERAMIDE, ITS PREPARATION AND SURGICAL DEVICES FABRICATED THEREFROM

This application claims benefit of Provisional Application Number 60/036,536 filed Jan. 28, 1997.

TECHNICAL FIELD

An absorbable polyesteramide, its preparation and absorbable surgical devices fabricated therefrom such as monofilament and multifilament sutures, films, sheets, plates, clips, staples, pins, screws, and the like are described herein.

BACKGROUND

Polyesteramides are polymers containing both ester linkages and amide linkages. Their significance for technology of surgical devices stems from the fact that the susceptibility of their ester linkages to hydrolysis confers upon them the ability to be eventually absorbed, or resorbed by a body into which they have been implanted and their amide linkages confer upon them the desirable mechanical properties characteristic of polyamides.

Fiber-forming polyesteramides obtained from the single stage reaction of approximately equimolar amounts of a monoalkanolamine and a dicarboxylic acid are known from U.S. Pat. No. 2,386,454. Polyesteramides indicated to be useful for the manufacture of absorbable sutures and other surgical devices are disclosed in U.S. Pat. No. 4,226,243 as obtained from the reaction of a bis-oxyamidodiol (itself derived from the reaction of diethyl oxalate with a monoalkanolamine such as ethanolamine) with a dicarboxylic acid ester. U.S. Pat. No 4,343,931 discloses absorbable surgical devices manufactured from polyesteramides obtained by reacting a diamide with lactic or glycolic acid to produce a diamidediol, which is then reacted with a bischloroformate or a compound selected from the group consisting of dicarboxylic acids, diacidchlorides and dicarboxylic acid anhydrides.

Nylon refers to a family of high strength, resilient synthetic materials, the long chain molecules of which contain recurring amide groups. Articles made from Nylon have been widely accepted for a variety of applications. Certain surgical applications, however, require a surgical device that is bioabsorbable. Nylon is not bioabsorbable and is therefore unacceptable in such circumstances.

It would be desirable to provide a surgical device material that has strength and resiliency characteristics equivalent to those of nylon, but which is bioabsorbable.

SUMMARY

A biodegradable polyesteramide is provided having units of the following formula:

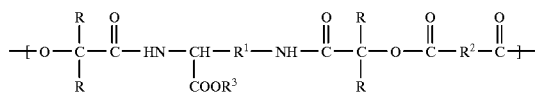

in which R is hydrogen, methyl or ethyl;

$R^1$ and $R^2$ may be identical or different and are selected from the group consisting of linear alkyl, branched alkyl, linear alkylene, branched alkylene, oxa-alkylene, cycloalkylene and arylene; and $R^3$ may be hydrogen, linear or branched alkyl, or linear or branched alkylene.

A method of making biodegradable polyesteramide is provided which includes reacting an amino alkyl ester with alpha hydroxy acid to form diamide-diol and reacting diamide-diol with acyl halide to form the polyesteramide.

A surgical implant including a biocompatible polyesteramide is also provided.

DETAILED DESCRIPTION OF THE PREFERRED EMBODIMENTS

The polyesteramide herein is biodegradable and in certain aspects biocompatible and suitable for use in medicine. Such polyesteramides combine the good mechanical properties of polyamides with the degradability of polyesters.

Polyesteramides in accordance with the present disclosure have the following formula:

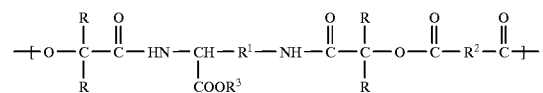

in which R is hydrogen, methyl or ethyl;

$R^1$ and $R^2$ may be identical or different and are selected from the group consisting of linear alkyl, branched alkyl, linear alkylene, branched alkylene, oxa-alkylene, cycloalkylene and arylene; and $R^3$ may be hydrogen, linear or branched alkyl, or linear or branched alkylene.

To obtain such polyesteramide, diamino alkyl ester is reacted with alpha hydroxy acid in the presence of suitable solvent and suitable acid such as aromatic sulfonic acid, an aliphatic acid and inorganic acid, at elevated temperatures to yield diamide-diol. The diamide-diol is converted into a bioabsorbable polymer by reaction with a diacyl halide or dicarboxylic acid.

Suitable amino acid esters include lysine alkyl esters such as lysine methyl ester and lysine ethyl ester. Suitable hydroxyacids include glycolic acid and lactic acid. Suitable solvents include toluene, acetonitrile, methylene chloride and chloroform. Aromatic sulfonic acids which may be used include p-toluene sulfonic acid. Aliphatic acids which may be used include aceteic acid. Inorganic acids which may be used include hydrochloric acid and sulfuric acid.

A preferred method involves reacting about 1 mole of amino alkyl ester with about 2 moles of alpha hydroxy acid at a temperature of between about 100° C. and about 150° C. in toluene and about 1% to 5% by weight p-toluene sulfonic acid as a catalyst. Distillation may be used to remove excess water by-product.

The resulting diamide-diol is dissolved in a solvent which is non-reactive with diacyl halides or dicarboxylic acid and which has a boiling point of about 100° C. or higher. Suitable solvents include tolulene, xylene or chlorobenzene. The diamide-diol can be refluxed at elevated temperatures with equimolar amounts of diacyl halide or dicarboxylic acid. Reflux temperatures may range from about 100° C. to about 150° C. Chlorobenzene is a preferred solvent.

Preferred diacyl halides are diacyl chlorides of the following formula

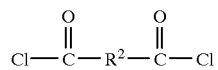

wherein R2 is selected from the group consisting of linear alkyl, branched alkyl, linear alkylene, branched alkylene, oxa-alkylene, cycloalkylene and arylene.

In a preferred aspect, diacyl chloride of the following formula is utilized:

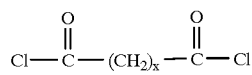

wherein X is a number ranging from 0 to 10.

Also suitable for use in place of diacyl halide are diacid dimethyl or diethyl esters of dicarboxylic acid. Dicarboxylic acids herein include methyl and ethyl esters thereof and acid chlorides and anhydrides thereof. Examples include, but are not limited to oxalic acid; malonic acid; succinic acid; 2,3-dimethylsuccinic acid; glutaric acid; 3,3-dimethylglutaric acid; 3-methyladipic acid; adipic acid; pimelic acid; suberic acid; azelaic acid; sebacic acid; 1,9-nonanedicarboxylic acid; 1,10-decanedicarboxylic acid; 1,11-undecanedicarboxylic acid; 1,12-dodecanedicar- boxylic acid, 1,13-tridecanedicarboxylic acid; 1,14-tetradecanedicarboxylic acid; 1,15-pentadecanedicarboxylic acid; 1,16-hexadecanedicarboxylic acid; maleic acid; trans-β-hydromuconic acid; fumaric acid; diglycolic acid; 3,3'-oxydipropionic acid; 4,4'-oxydibutyric acid; 4,5'-oxydivaleric acid; 6,6'-oxydicaproic acid; 8,8'-oxydicaprylic acid; 6-oxaundecanedioic acid; 5-oxaazelaic acid; 5-oxadodecanedioic acid; 5-oxatetradecanedioic acid; 5-oxahexadecanedioic acid; 6-oxadodecanedioic acid; 6-oxatridecanedioic acid; 6-oxapentadecanedioic acid; 6-oxaheptadecanedioic acid; 7-oxapentadecanedioic acid; 10-oxanonadecanedioic acid and other oxa-aliphatic dicarboxylic acids; phthalic acid; isophthalic acid; tetrephthalic acid and other aromatic dicarboxylic acids; 1,2-cyclobutanedicarboxylic-acid; and 1,4-cyclohexanedicarboxylic acid.

In a preferred aspect, the reaction may be illustrated as follows:

be used to fabricate degradable containers and packaging materials which can degrade in landfills in contrast to nondegradable materials which present environmental concerns.

Optional additives which may be present in compositions made from the polyesteramides described herein include plasticizers, release agents and other processing acids. Where the composition is used to make a surgical device, stearic acid or calcium stearate are particularly useful additives due to their biocompatibility.

The polyesteramides can be formed into surgical articles using any known technique, such as, for example, extrusion, molding and/or solvent casting. The polyesteramides can be used alone, blended with other absorbable compositions, or in combination with non-absorbable components. As mentioned above, a wide variety of surgical articles can be manufactured from the polyesteramides described herein. Fibers made from the present polyesteramides can be knitted or woven with other fibers, either absorbable or nonabsorbable to form meshes or fabrics. Compositions including these polyesteramides can also be used as an absorbable coating for surgical devices.

In an alternative embodiment, the polyesteramides described herein are admixed with a filler. The filler can be in any particulate form, including granulate and staple fibers. While any known filler may be used, hydroxyapatite, tricalcium phosphate, bioglass or other bioceramics are the preferred fillers. Normally, from about 10 grams to about 400 grams of filler are mixed with 100 grams of polymer. The filled, cross-linked polymers are useful, for example, as a molding composition.

In another aspect, compositions containing the polyester amides described herein can be used to make reinforced composites. Thus, for example, the polyesteramide composition can form the matrix of the composite and can be reinforced with bioabsorbable or non-absorbable fibers or particles. Alternatively, a matrix of any bioabsorbable or

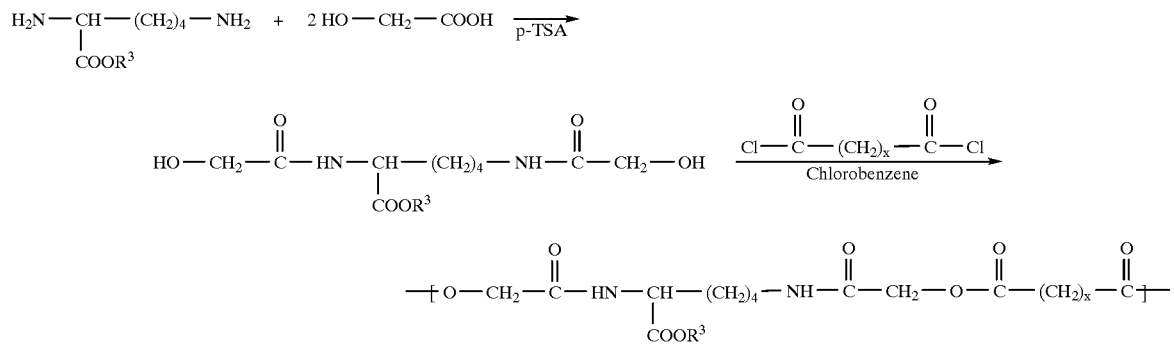

wherein $R^3$ is $CH_3$ or $CH_2CH_3$ and X is a number ranging from 0 to 10.

The degradable polyesteramide herein is suitable for use in a wide variety of applications. Since the degradation products of the biocompatable polymer herein are non-toxic, it is suitable for biomedical uses. For example, depending on the number of ester linkages in the polymeric chain, the polymer can be made to degrade slowly and can thus be utilized for fabricating long term implantable surgical materials. Examples of implants include prosthetic devices, sutures, staples, clips and other fasteners, screws, pins, films, meshes, drug delivery devices, anastomosis rings, surgical dressings and the like. The polyesteramides herein may also non-bioabsorbable polymer composition can be reinforced with fibers or particulate material made from compositions containing the polyesteramides described herein.

It is further contemplated that one or more medico-surgically useful substances can be incorporated into compositions containing the polyesteramides described herein. Examples of such medico-surgically useful substances include, for example, those which accelerate or beneficially modify the healing process when particles are applied to a surgical repair site. So, for example, articles made from compositions containing the present polyesteramides can carry a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, one or several growth promoting factors can be introduced into the articles, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system. It is also contemplated that medico-surgically useful substances can include non-therapeutic agents such as dyes, which typically do not exert biological activity per se.

It is contemplated that it may be desirable to dye articles made from compositions containing the present polyesteramides in order to increase visibility of the article in the surgical field. Dyes, such as those known to be suitable for incorporation in sutures, can be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979). Preferably, sutures in accordance with this disclosure are dyed by adding up to about a few percent and preferably about 0.2% dye to the resin composition prior to extrusion.

It will be understood that various modifications may be made to the embodiments disclosed herein. Therefore the above description should not be construed as limiting, but merely as exemplifications of preferred embodiments. Those skilled in the art will envision other modifications within the scope and spirit of the claims appended hereto.

What is claimed is:

1. A polymer comprising polyesteramide units of the following formula:

$$-\!\!\left[\!\operatorname{O}-\underset{\underset{R}{|}}{\overset{\overset{R}{|}}{C}}-\overset{\overset{O}{\|}}{C}-\operatorname{HN}-\underset{\underset{COOR^3}{|}}{\overset{}{C}H}-R^1-\operatorname{NH}-\overset{\overset{O}{\|}}{C}-\underset{\underset{R}{|}}{\overset{\overset{R}{|}}{C}}-\operatorname{O}-\overset{\overset{O}{\|}}{C}-R^2-\overset{\overset{O}{\|}}{C}\!\right]\!\!-$$

wherein R is selected from the group consisting of hydrogen, methyl and ethyl;
   $R^1$ and $R^2$ is identical or different, and are selected from the group consisting of linear alkyl, branched alkyl, linear alkylene, branched alkylene, oxa-alkylene, cycloalkylene and arylene; and
   $R^3$ is selected from the group consisting of hydrogen, linear alkyl, branched alkyl, linear alkylene, and branched alkylene.

2. A surgical implant comprising a biocompatible polyesteramide including units of the following formula:

$$-\!\!\left[\!\operatorname{O}-\underset{\underset{R}{|}}{\overset{\overset{R}{|}}{C}}-\overset{\overset{O}{\|}}{C}-\operatorname{HN}-\underset{\underset{COOR^3}{|}}{\overset{}{C}H}-R^1-\operatorname{NH}-\overset{\overset{O}{\|}}{C}-\underset{\underset{R}{|}}{\overset{\overset{R}{|}}{C}}-\operatorname{O}-\overset{\overset{O}{\|}}{C}-R^2-\overset{\overset{O}{\|}}{C}\!\right]\!\!-$$

wherein R is selected from the group consisting of hydrogen, methyl and ethyl;
   $R^1$ and $R^2$ is identical or different, and are selected from the group consisting of linear alkyl, branched alkyl, linear alkylene, branched alkylene, oxa-alkylene, cycloalkylene and arylene; and
   $R^3$ is selected from the group consisting of hydrogen, linear alkyl, branched alkyl, linear alkylene and branched alkylene.

3. A surgical implant according to claim 2 wherein the implant is bioabsorbable.

4. A surgical implant according to claim 2 wherein the implant is selected from the group consisting of suture, staple, clip, screws, pin, film, sheet, mesh, drug delivery device and prosthetic device.

5. A method of making a degradable polyesteramide comprising:
   reacting amino alkyl ester with alphahydroxy acid to form diamide-diol; and
   reacting diamide-diol with diacyl-halide or dicarboxylic acid to form polyesteramide.

6. A method of making a biodegradable polyesteramide according to claim 5 wherein amino alkyl ester is lysine alkyl ester.

7. A method of making a biodegradable polyesteramide according to claim 5 wherein the alphahydroxy acid is selected from the group consisting of glycolic acid and lactic acid.

8. A method of making a biodegradable polyesteramide according to claim 5 wherein the diamide-diol includes the following structure:

$$\operatorname{HO}-\underset{\underset{R}{|}}{\overset{\overset{R}{|}}{C}}-\overset{\overset{O}{\|}}{C}-\operatorname{HN}-\underset{\underset{COOR^3}{|}}{\overset{}{C}H}-R^1-\operatorname{NH}-\overset{\overset{O}{\|}}{C}-\underset{\underset{R}{|}}{\overset{\overset{R}{|}}{C}}-\operatorname{OH}$$

wherein R is selected from the group consisting of hydrogen, methyl and ethyl;
   $R^1$ is selected from the group consisting of linear alkyl, branched alkyl, linear alkylene, branched alkylene, oxa-alkylene, cycloalkylene and arylene; and
   $R^3$ is selected from the group consisting of hydrogen, linear alkyl, branched alkyl, linear alkylene and branched alkylene.

9. A method of making a biodegradable polyesteramide according to claim 5 wherein the diacyl halide is diacyl chloride.

10. A method of making a biodegradable polyesteramide according to claim 9 wherein the diacyl chloride has the following structure:

$$\operatorname{Cl}-\overset{\overset{O}{\|}}{C}-R^2-\overset{\overset{O}{\|}}{C}-\operatorname{Cl}$$

wherein $R^2$ is selected from the group consisting of linear alkyl, branched alkyl, linear alkylene, branched alkylene, oxa-alkylene, cycloalkylene and arylene.

11. A biodegradable polyesteramide manufactured by reacting lysine alkyl ester with alpha hydroxy acid to form diamide-diol and reacting diamide-diol with diacyl halide to form polyesteramide.

12. A biodegradable polyesteramide according to claim 11 wherein amino alkyl ester is lysine alkyl ester.

13. A biodegradable polyesteramide according to claim 11 wherein the alphahydroxy acid is selected from the group consisting of glycolic acid and lactic acid.

14. A biodegradable polyesteramide according to claim 11 wherein the diamide-diol includes the following structure:

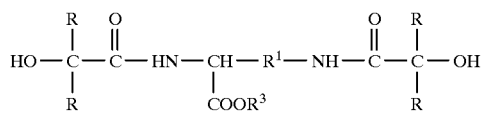

wherein R is selected from the group consisting of hydrogen, methyl and ethyl;

$R^1$ is selected from the group consisting of linear alkyl, branched alkyl, linear alkylene, branched alkylene, oxa-alkylene, cycloalkylene and arylene; and $R^3$ is selected from the group consisting of hydrogen, linear alkyl, branched alkyl linear alkylene and branched alkylene.

15. A biodegradable polyesteramide according to claim 11 wherein the diacyl halide is diacyl chloride.

16. A biodegradable polyesteramide according to claim 15 wherein the diacyl chloride has the following structure:

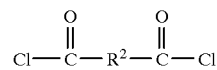

wherein $R^2$ is selected from the group consisting of linear alkyl, branched alkyl, linear alkylene, branched alkylene, oxa-alkylene, cycloalkylene and arylene.

* * * * *